US010304220B2

(12) United States Patent
Wang

(10) Patent No.: US 10,304,220 B2
(45) Date of Patent: May 28, 2019

(54) ANATOMY SEGMENTATION THROUGH LOW-RESOLUTION MULTI-ATLAS LABEL FUSION AND CORRECTIVE LEARNING

(71) Applicant: INTERNATIONAL BUSINESS MACHINES CORPORATION, Armonk, NY (US)

(72) Inventor: Hongzhi Wang, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 127 days.

(21) Appl. No.: 15/253,326

(22) Filed: Aug. 31, 2016

(65) Prior Publication Data

US 2018/0061091 A1    Mar. 1, 2018

(51) Int. Cl.

| G06K 9/00 | (2006.01) |
|---|---|
| G06T 11/00 | (2006.01) |
| G06K 9/62 | (2006.01) |
| G06K 9/66 | (2006.01) |
| A61B 6/03 | (2006.01) |
| G06T 7/30 | (2017.01) |
| G06T 7/11 | (2017.01) |

(52) U.S. Cl.
CPC ............ *G06T 11/008* (2013.01); *A61B 6/032* (2013.01); *G06K 9/6202* (2013.01); *G06K 9/66* (2013.01); *G06T 7/11* (2017.01); *G06T 7/30* (2017.01); *G06T 2207/10081* (2013.01); *G06T 2207/20081* (2013.01); *G06T 2207/30048* (2013.01)

(58) Field of Classification Search
CPC ... G06T 11/008; G06T 7/0024; G06T 7/0081; A61B 6/032; G06K 9/6202; G01R 33/56; H04N 1/4172

USPC ........................................................ 382/131
See application file for complete search history.

(56) References Cited

U.S. PATENT DOCUMENTS

| 7,676,065 | B2 * | 3/2010 | Wiedemann ......... G06K 9/0063 382/103 |
|---|---|---|---|
| 9,014,465 | B2 | 4/2015 | Metaxas et al. |
| 9,076,238 | B2 | 7/2015 | Wu et al. |
| 2005/0100208 | A1 * | 5/2005 | Suzuki .................... G06T 5/007 382/157 |
| 2007/0081706 | A1 * | 4/2007 | Zhou .................... G06F 19/321 382/128 |
| 2011/0179044 | A1 * | 7/2011 | Crum .................... G06K 9/342 707/749 |

(Continued)

OTHER PUBLICATIONS

Andrew J.Asman et al., "Multi-atlas learner fusion: An efficient segmentation approach for large-scale data," Medical Image Analysis 26 (2015), p. 82-91.

(Continued)

*Primary Examiner* — Van D Huynh
(74) *Attorney, Agent, or Firm* — Erik A. Huestis; Stephen J. Kenny; Foley Hoag LLP

(57) ABSTRACT

Computationally efficient anatomy segmentation through low-resolution multi-atlas label fusion and corrective learning is provided. In some embodiments, an input image is read. The input image has a first resolution. The input image is downsampled to a second resolution lower than the first resolution. The downsampled image is segmented into a plurality of labeled anatomical segments. Error correction is applied to the segmented image to generate an output image. The output image has the first resolution.

16 Claims, 18 Drawing Sheets

(56) References Cited

U.S. PATENT DOCUMENTS

| | | | | |
|---|---|---|---|---|
| 2012/0300227 | A1* | 11/2012 | Ohk | G06K 9/38 |
| | | | | 358/1.2 |
| 2012/0324397 | A1* | 12/2012 | Patz | G06F 19/321 |
| | | | | 715/800 |
| 2013/0028538 | A1* | 1/2013 | Simske | 382/300 |
| 2013/0217996 | A1 | 8/2013 | Finkelstein et al. | |
| 2016/0364626 | A1* | 12/2016 | Sasaki | G06K 9/4671 |
| 2017/0086780 | A1* | 3/2017 | Sokulin | G06F 19/00 |
| 2017/0231550 | A1* | 8/2017 | Do | G06T 7/11 |
| | | | | 382/128 |
| 2017/0238907 | A1* | 8/2017 | Kommu Chs | A61B 8/483 |

OTHER PUBLICATIONS

P. Aljabar et al.,"Multi-atlas based segmentation of brain images: Atlas selection and its effect on accuracy," NeuroImage 46 (2009) p. 726-738.

Gerard Sanroma et al., " Learning to Rank Atlases for Multiple-Atlas Segmentation," IEEE Transactions on Medical Imaging, vol. 33, No. 10, Oct. 2014.

Hongzhi Wang and Paul A. Yushkevich, "Multi-atlas segmentation with joint label fusion and corrective learning—an open source implementation," Frontiers in Neuroinformatics, Nov. 2013, vol. 7, Article 27.

Torsten Rohlfing et al., "Evaluation of atlas selection strategies for atlas-based image segmentation with application to confocal microscopy images of bee brains," NeuroImage 21 (2004) 1428-1442.

\* cited by examiner

ANATOMY SEGMENTATION THROUGH LOW-RESOLUTION MULTI-ATLAS LABEL FUSION AND CORRECTIVE LEARNING

BACKGROUND

Embodiments of the present invention relate to anatomy segmentation, and more specifically, to computationally efficient anatomy segmentation through low-resolution multi-atlas label fusion and corrective learning.

BRIEF SUMMARY

According to embodiments of the present disclosure, methods of, and computer program products for, anatomy segmentation are provided. An input image is read. The input image has a first resolution. The input image is downsampled to a second resolution lower than the first resolution. The downsampled image is segmented into a plurality of labeled anatomical segments. Error correction is applied to the segmented image to generate an output image. The output image has the first resolution.

According to other embodiments of the present disclosure, methods of, and computer program products for, anatomy segmentation are provided. A target image and each one of a series of training images are resampled from an original resolution to a lower resolution. After resampling, the target image is compared against each one of the series of training images, through registration and warping, thereby producing a labeled target image for each of the training images. The labeled target images are weighted-averaged to form a consensus labeled target image. The consensus labeled target image is resampled from an original resolution to a higher resolution. Error correction is applied to the consensus labeled target image, thereby forming a finalized labeled target image.

DETAILED DESCRIPTION

Figure 1A:
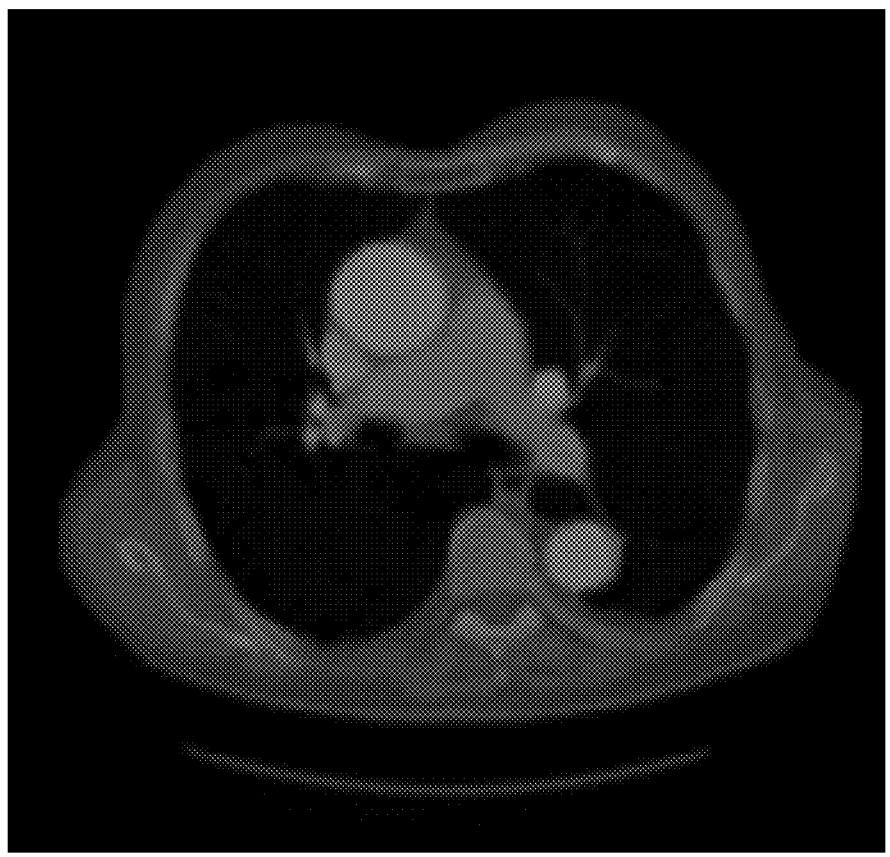
FIG. 1A is an exemplary unlabeled CT image.

Deformable registration based multi-atlas segmentation is suitable for a broad range of anatomy segmentation applications. However, this performance comes with a high computational burden due to the requirement for deformable image registration and voxel-wise label fusion. To address the high computational cost problem, the present disclosure provides for application of multi-atlas segmentation in low resolution space followed by refinement of the results by learning-based error correction in the native image space. In a cardiac CT segmentation application, methods according to the present disclosure not only significantly reduce the computational cost for deformable registration-based multi-atlas segmentation, but also produce more accurate segmentation.

Multi-atlas segmentation applies image registration to propagate anatomical labels from pre-labeled atlases to a target image and applies label fusion to resolve conflicting anatomy labels produced by warping multiple atlases. For anatomical structures that can be aligned across subjects through image registration, multi-atlas segmentation that employs deformable image registration for label propagation is one of the most competitive anatomy segmentation techniques.

Despite the segmentation performance, the high computational cost is a limiting factor on application of the technique to large scale problems. This problem is partially addressed by the increasing cost-effective computational powers brought by high performance computing technologies. When pairwise image registrations between each atlas and a target image can be computed fully in parallel, the overall turnaround for applying multi-atlas segmentation to segment one image equals the time for a single deformable registration plus the time for label fusion. However, both deformable image registration and label fusion still can take hours on processing a 3D volume data.

In order to make multi-atlas segmentation more suitable for large scale studies, addressing its high computational cost is necessary. For example, atlas selection may be applied for improving the speed and accuracy of label fusion. To address the high computational cost raised from employing deformable image registration, nonlocal label fusion techniques are developed to only work with affine/linear registrations for brain tissue segmentation problems. However, affine/linear registration is often inadequate for applications where large non-linear deformations exist, such as applications in cardiac and abdominal regions.

A reduction in the total number of registrations required for each segmentation task may also reduce the overall computation time. For example, machine learning may be applied to predict the accuracy of deformable registration between a pair of images based on the affine registration between them. In this way, effective atlas selection based on affine registrations may be achieved, and deformable registration is only necessary for the selected atlases. Alternatively, both atlases and testing images may be registered and warped into a common template space. In this way, only one deformable registration is required at the testing stage.

One drawback of various fast label propagation techniques is the inferior accuracy. Hence, such approaches obtain speed improvement by sacrificing segmentation accuracy. Various techniques such as those described above may be combined with fast label propagation, but such combinations do not mitigate the loss in accuracy.

In order to address the computation issue, various methods according to the present disclosure combine multi-atlas segmentation with learning-based segmentation. In general, learning-based segmentation is faster, but less accurate than multi-atlas segmentation. However, when applied to correct errors produced by multi-atlas segmentation, learning-based segmentation produces accurate segmentation as well. According to various methods herein, the computational burden is reduced by performing multi-atlas segmentation with pairwise deformable registration in a downsampled coarse scale space, followed by learning-based error correction in the original space.

As set forth below, performance of multi-atlas segmentation may vary at different scales and the native scale may not be optimal for producing the most accurate segmentation. Applying multi-atlas segmentation in a coarse scale followed by learning-based error correction in the native scale space can significantly reduce the overall computational cost, without sacrificing segmentation accuracy. In order to maximally utilize the information provided from images, image analysis is usually conducted either in the native acquisition space or in a space close to the acquisition space. However, working in a downsampled space may still be preferable in some circumstances, as described further herein.

Since the computational cost and memory requirement for both deformable image registration and label fusion are proportional to the size of the processed image, one immediate advantage of applying multi-atlas segmentation in a downsampled coarse scale space is the speed improvement and memory reduction. Furthermore, working in a coarse scale may be beneficial for labeling some anatomical structures as well. Different anatomical structures may be best distinguishable at different scales. For example, clinicians often need to switch the image viewer at different scales for determining the boundaries of certain anatomy structures. In general, working in low resolution may be optimal for labeling large scale anatomical structures, while high resolution may be more suitable for labeling small scale structures.

Image downsampling is an information loss process. Hence, multi-atlas segmentation in a coarse resolution space potentially may cause additional errors. For example, as shown in FIG. 2C, discussed further below, the anatomy boundaries produced in low resolution space are too coarse to align accurately with the anatomy boundary in the original image space. However, since resolution change is a systematic change, such errors can be effectively corrected by learning-based error correction, as described below.

In order to apply multi-atlas segmentation in a low resolution space, all training images and their segmentations are downsampled to have the same coarse spatial resolution. Given a testing image, it is downsampled into the target spatial resolution as well. After applying image registration and label fusion in the low resolution space, the produced results are resampled back to the native space of the testing image.

Automatic segmentation algorithms may produce systematic errors in comparison to the gold standard manual segmentation. Such systematic errors may be produced due to the limitations of the segmentation model employed by the method or due to suboptimal solutions produced by the optimization algorithm. Systematic errors may also be produced due to the fact that segmentation is produced in a low resolution space. To reduce such systematic errors, corrective learning according to embodiments of the present disclosure applies machine learning techniques to automatically detect and correct systematic errors produced by a host automatic segmentation method.

Various corrective learning algorithms are suitable for use according to the present disclosure, including those available through the Advanced Normalization Tools (ANTs) project. In some embodiments, a random forest classifier is used. In other embodiments, an adaboost classifier is used. Corrective learning can be naturally combined with multi-atlas segmentation because no additional training images other than the atlases are required. For each training image, its low resolution multi-atlas segmentation is produced by using the remaining training images as the atlases.

Subject images may be acquired using a variety of imaging devices known in the art. For example, cardiac CT studies may be acquired by a Siemens CT Scanner such as the SOMATOM Definition Flash. In the examples herein, CT images are axially acquired. Each image has isotropic in-plane resolutions, varying from 0.55 mm$^2$ to 0.80 mm$^2$. The slice thickness varies from 0.8 mm to 2.0 mm. A histogram equalization is applied to each image to standardize the intensity scale. The histogram equalized images are then resampled to have a 1 mm$^3$ isotropic resolution.

Figure 1B:
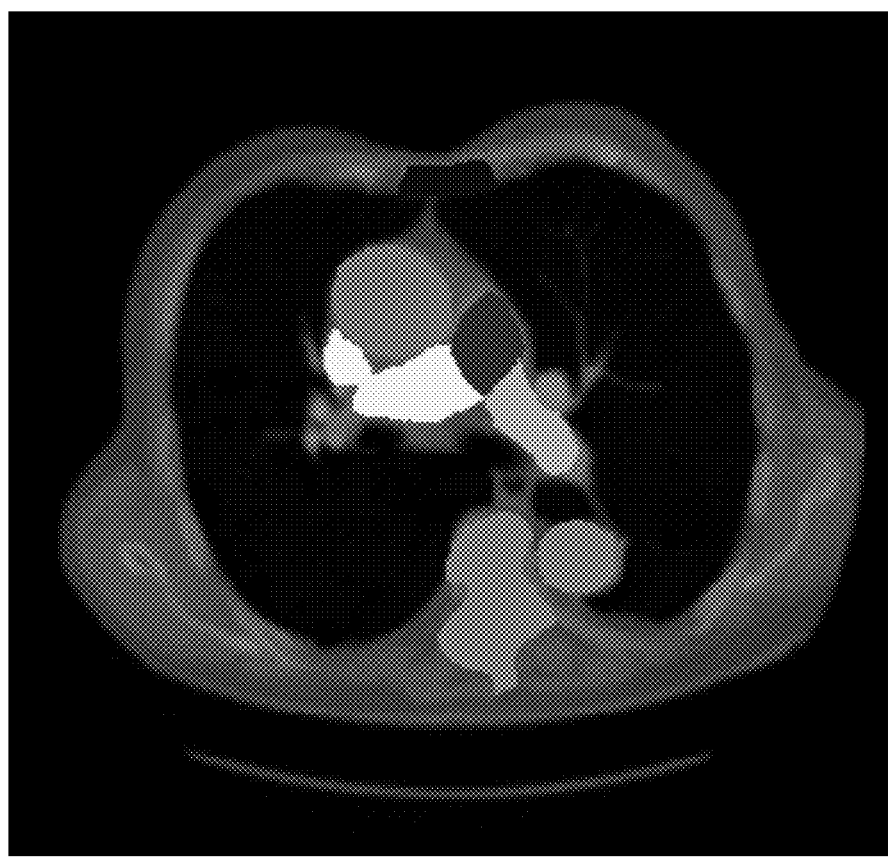
FIG. 1B depicts an exemplary manual labelling of the image of FIG. 1A.

Referring to FIG. 1, an exemplary CT image is shown. The base image of FIG. 1A is manually traced by a clinician using existing commercial software to yield labeled FIG. 1B. In this example, Amira is used to label for 28 cases: sternum, aorta (ascending/descending/arch/root), pulmonary artery (left/right/trunk), vertebrae, left/right atrium, left/right ventricle, left ventricular myocardium, superior/inferior vena cava, and aortic/tricuspid/pulmonary/mitral valve.

In the following summary of an exemplary implementation, multi-atlas segmentation in two isotropic low spatial resolutions, 3 mm$^3$ and 5 mm$^3$, respectively are examined. Each image and its manual segmentation are resampled into the two spatial resolutions. For each of the three resolutions, a four-fold cross validation on the 28 cases is conducted. For each cross-validation test, 7 images are selected for testing and the remaining 21 images are applied as training images, i.e., atlases. The reported results are averaged from the four cross-validation experiments.

The image-based registration is computed using the Advanced Normalization Tools (ANTs) software. The registration sequentially optimizes an affine transform and a deformable transform (Syn) between the pair of images, using the Mattes mutual information metric. The gradient step is set to 0.1. Three resolution levels with maximum 200 iterations at the coarse level, 100 iterations at the middle level and 50 iterations at the finest level are applied. With these parameters, registering a pair of images at the native 1 mm resolution (~300×300×200 image size) takes about 4 hours. Registering a pair of images at 3 mm (~100×100×70) and 5 mm (~60×60×40) resolutions takes about 203 and 54 seconds, respectively.

Image similarity based local weighted voting is applied for combining the candidate segmentations produced by different atlases for the same target image. The voting weights are computed using the joint label fusion technique. The joint label fusion software distributed from ANTs is applied with the default parameters. The produced low resolution segmentation is then resampled back to 1 mm resolution. Applying joint label fusion using 20 atlases to process one image takes about 210 minutes at 1 mm resolution, 10 and 2.5 minutes at 3 mm and 5 mm resolution, respectively.

The dilation diameter is set to 5 mm for generating ROI for each label. Each random forest classifier is set to have 20 trees. The maximal depth of each tree is set to 20. With these parameters, the Java implementation takes about 20 minutes to process one image at the native 1 mm resolution.

In summary, the total processing time for applying 20 atlases to segment a single image at 1 mm, 3 mm, and 5 mm resolution is 5230 minutes, 98 minutes, and 40 minutes, respectively. Applying multi-atlas segmentation at 5 mm resolution followed by error correction in the native space is about 130 times faster than applying both multi-atlas segmentation and corrective learning at 1 mm resolution. If the twenty pairwise deformable registrations are computed fully in parallel, processing one image takes about 480 minutes, 33 minutes, and 23.5 minutes at the three resolutions, respectively. Working at the 5 mm resolution is about 20 times faster than working at 1 mm resolution.

Figure 2A:
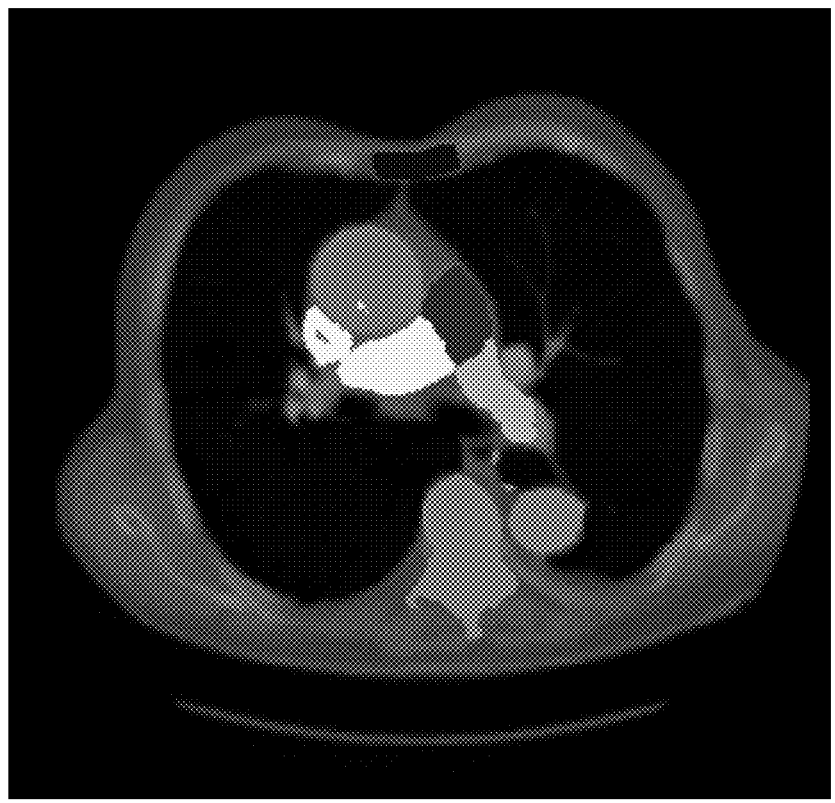
FIGS. 2A-C depict segmentations generated by multi-atlas label fusion at 1 mm, 3 mm, and 5 mm, respectively.
Figure 2B:
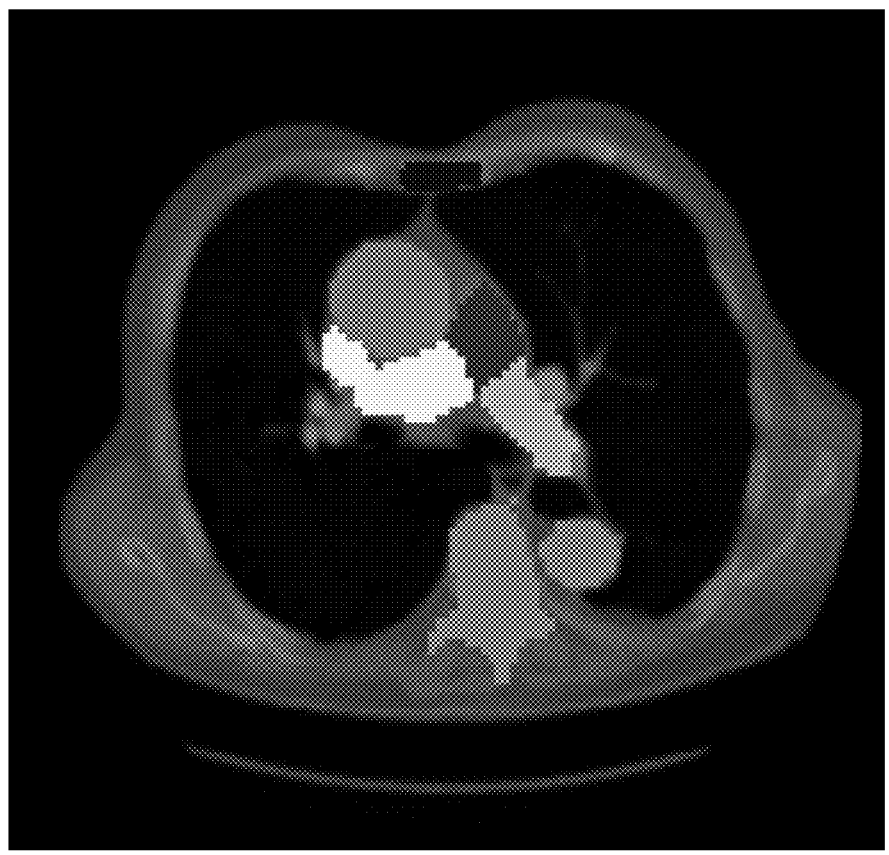
Figure 2C:
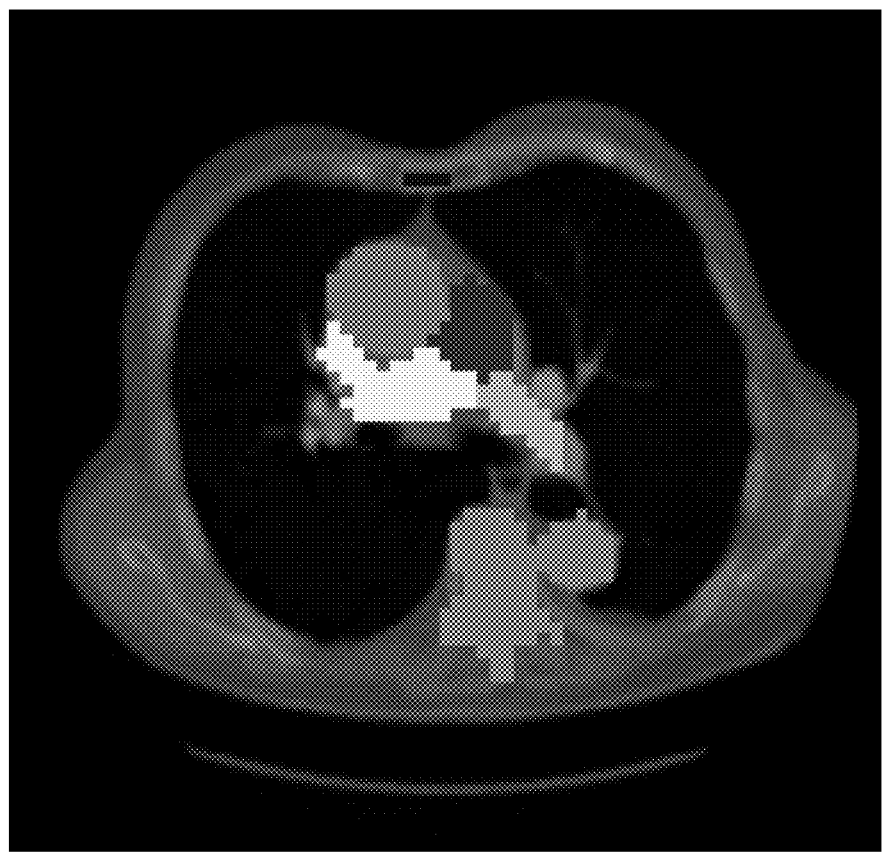

Referring to FIGS. 2A-C, segmentations produced by multi-atlas label fusion (MALF) in three spatial resolutions are shown for one subject. In FIG. 2A, the input image is downsampled to 1 mm resolution. In FIG. 2B, the input image is downsampled to 3 mm resolution. In FIG. 2C, the input image is downsampled to 5 mm resolution. It will be apparent that performing segmentation at lower resolutions results in unsuitably coarse labelling.

Figure 3A:
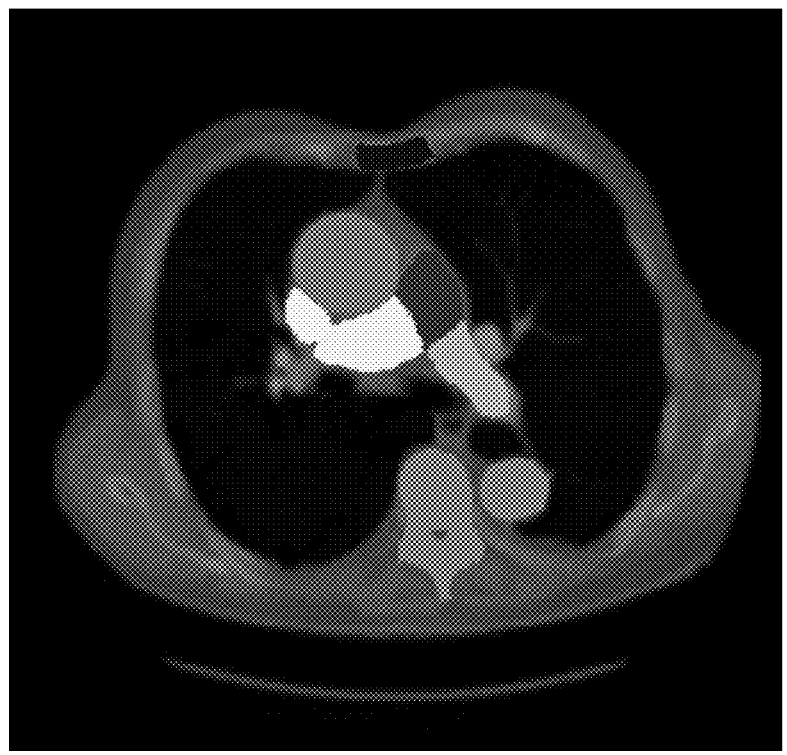
FIGS. 3A-C depict segmentations generated by multi-atlas label fusion with corrective learning at 1 mm, 3 mm, and 5 mm, respectively.
Figure 3B:
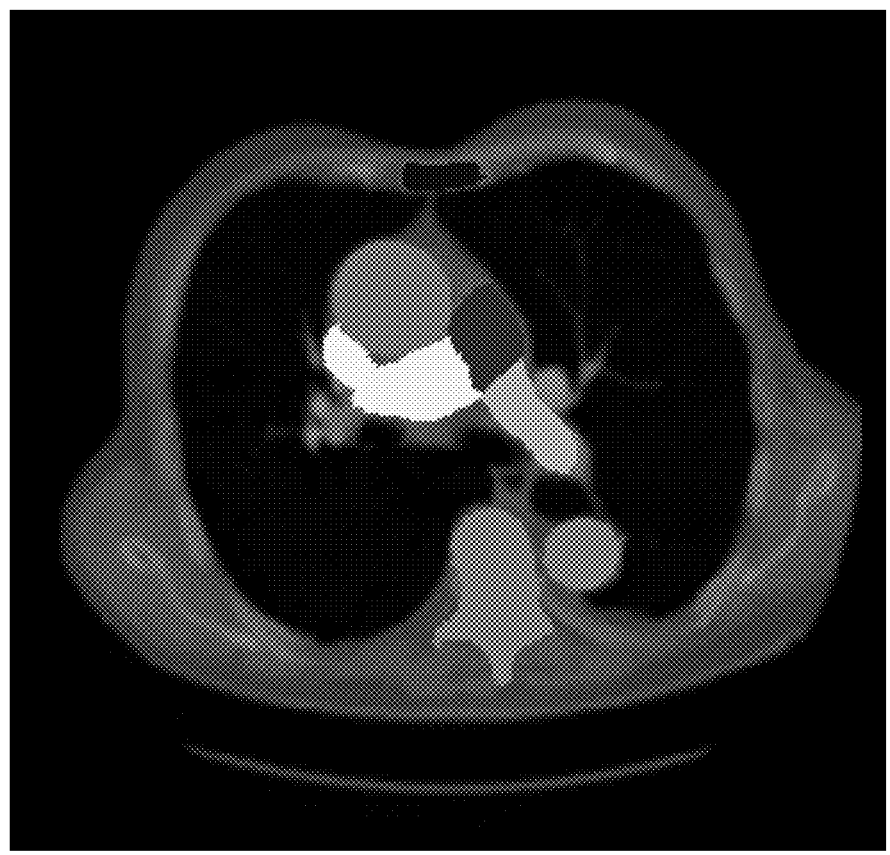
Figure 3C:
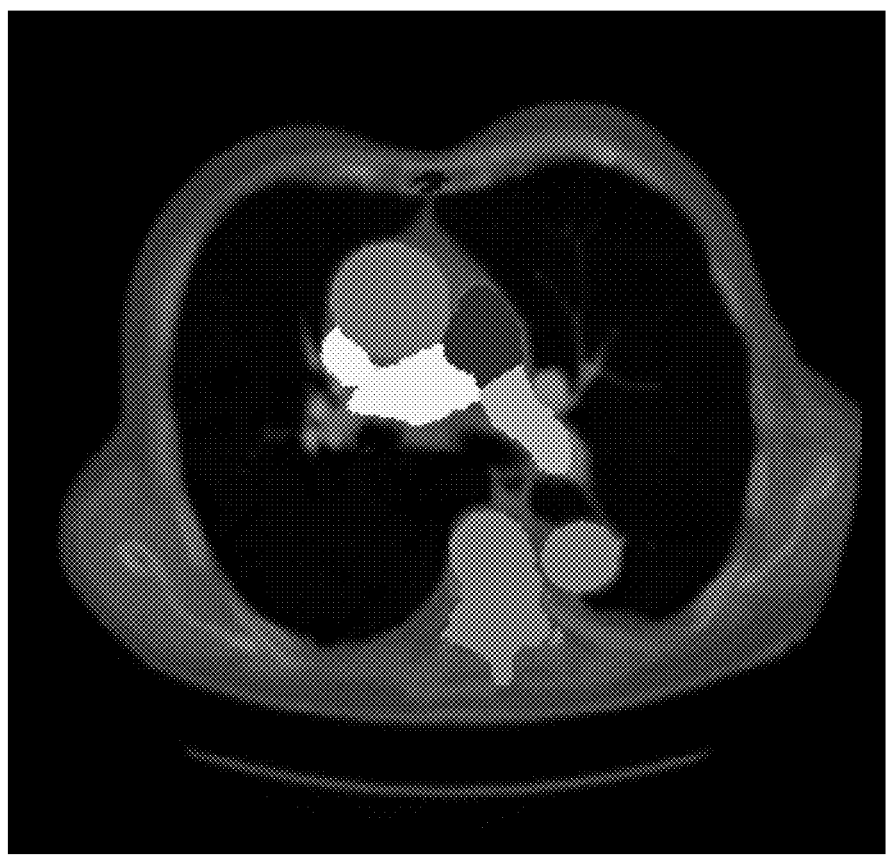

For comparison, FIGS. 3A-C show the segmentations produced by multi-atlas label fusion with learning-based error correction (MALF+CL) in three spatial resolutions for the same subject. In FIG. 3A, the input image is downsampled to 1 mm resolution before labeling. In FIG. 2B, the input image is downsampled to 3 mm resolution before labeling. In FIG. 2C, the input image is downsampled to 5 mm resolution before labeling.

Figure 4:
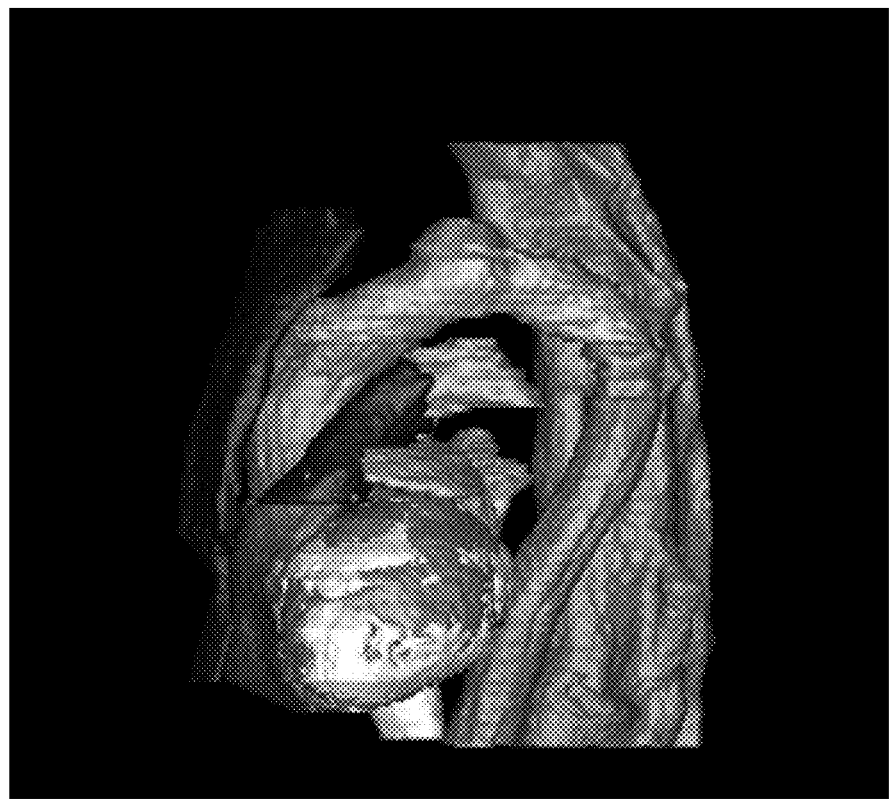
FIG. 4 is an exemplary manual labelling of a CT image.
Figure 5A:
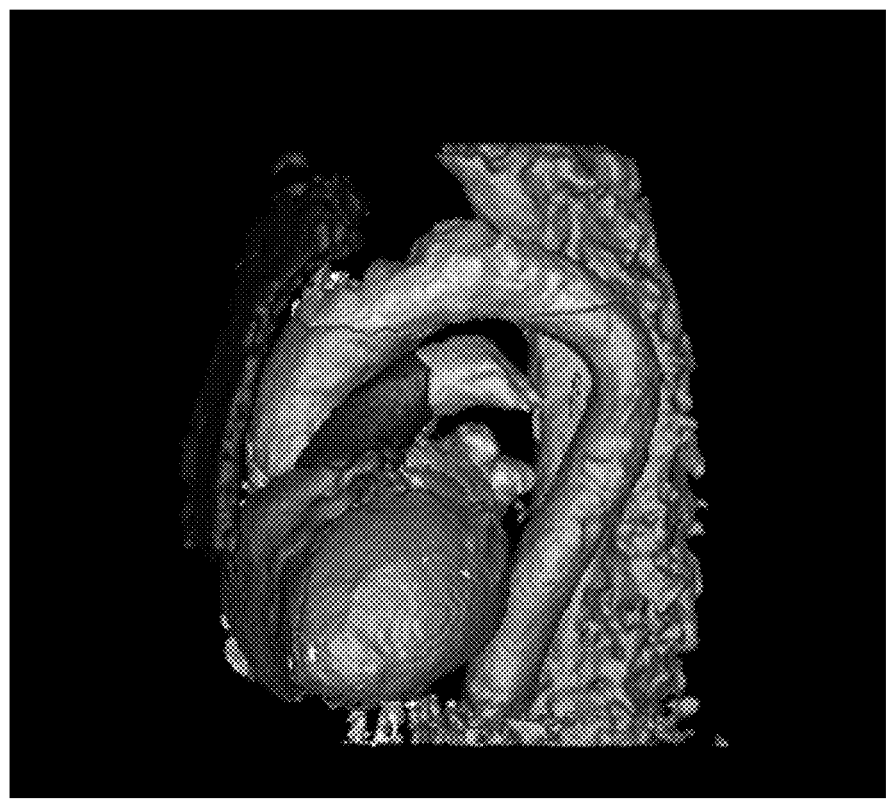
FIGS. 5A-C depict segmentations generated by multi-atlas label fusion at 1 mm, 3 mm, and 5 mm, respectively.
Figure 5B:
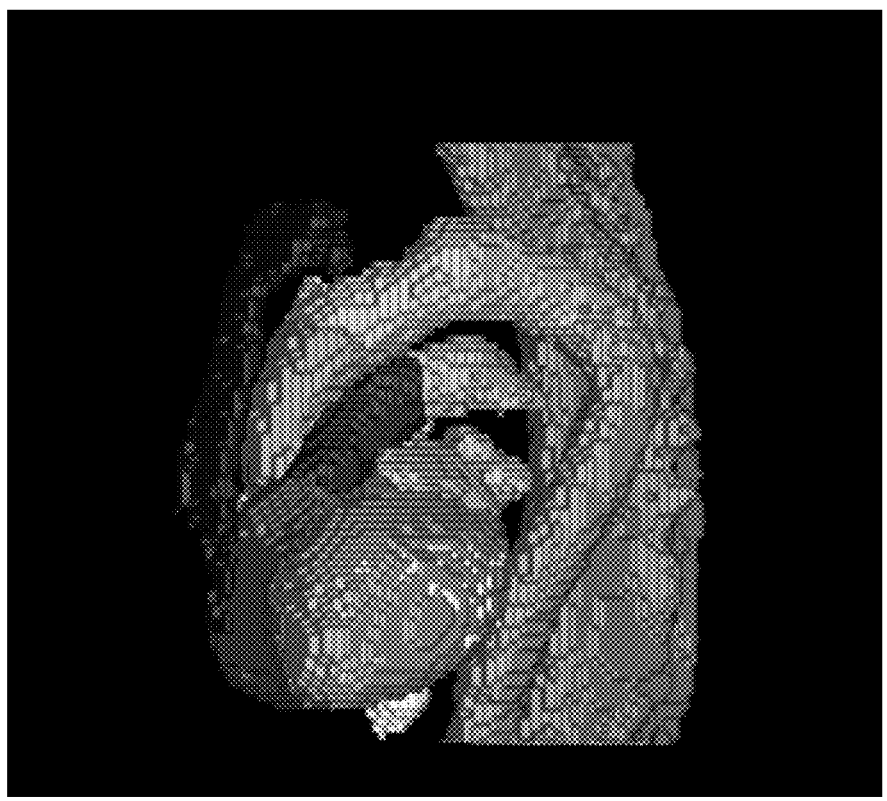
Figure 5C:
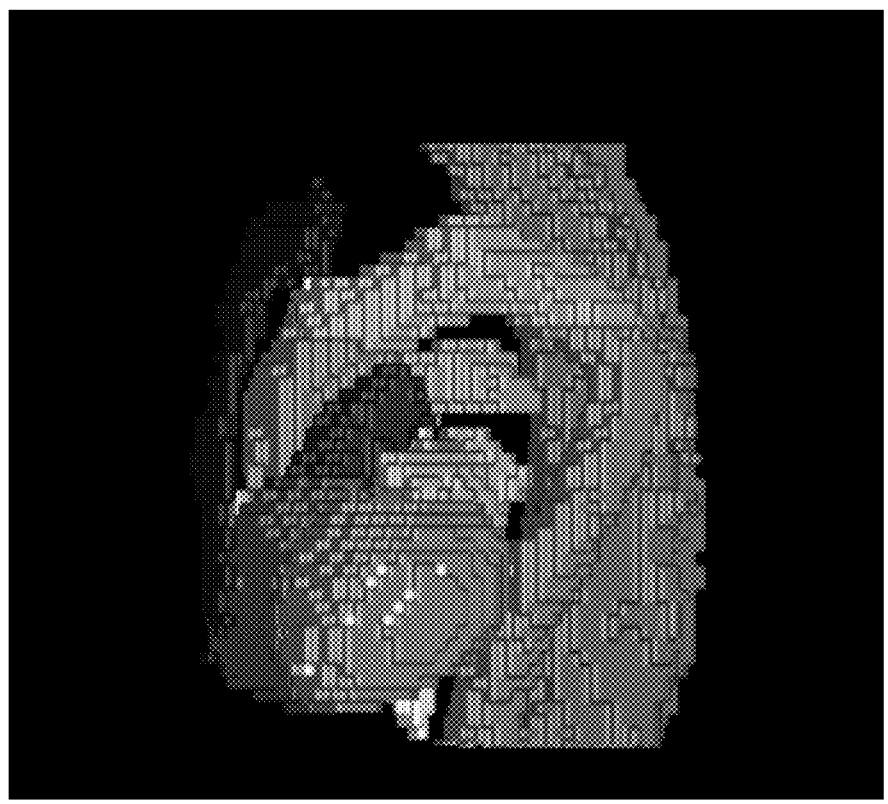

Referring to FIG. 4, a 3D surface rendering of the manual segmentations produced for the same subject is shown. FIGS. 5A-C shows the 3D surface rendering of the segmentations produced for the same subject at 1 mm, 3 mm, and 5 mm, respectively. The segmentations produced at 3 mm and 5 mm resolution have inaccurate boundaries. The stepwise boundaries are typical patterns obtained from upsampling from a low resolution to a high resolution.

Figure 6A:
FIGS. 6A-C depict segmentations generated by multi-atlas label fusion with corrective learning at 1 mm, 3 mm, and 5 mm, respectively.
Figure 6B:
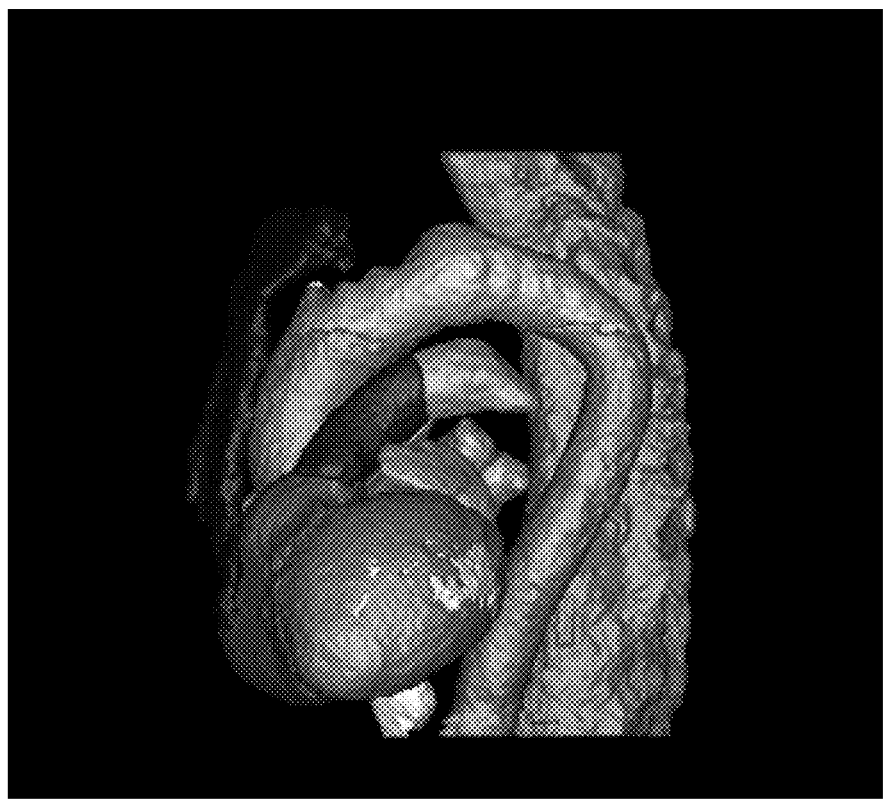
Figure 6C:
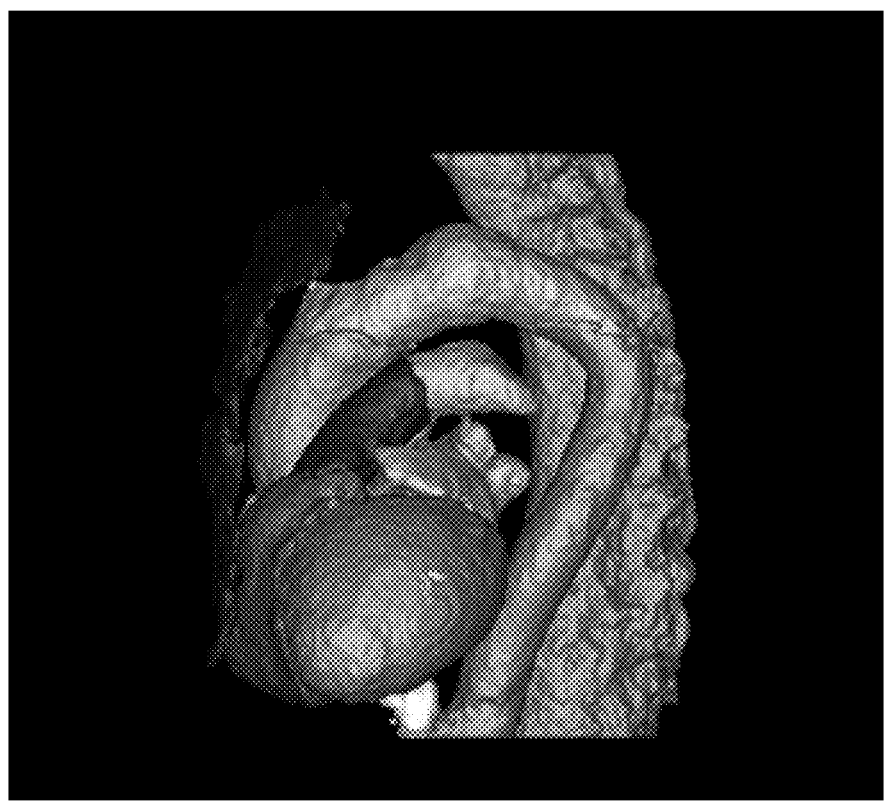

Referring to FIGS. 6A-C, this effect is completely removed after applying learning-based error correction. This result demonstrates that the inaccurate boundaries produced due to applying MALF in a downsampled space can be effectively corrected through learning-based error correction.

Table 1 summarizes segmentation accuracy produced by applying MALF at different spatial resolutions. The best performance is produced by downsampling the images to 3 mm resolution. One explanation is that image registration is more likely to be stuck in local optimal solutions when it is computed in a high resolution space. In finer resolution spaces, the searching range for correspondence matching is larger as the same amount of deformation will result in larger voxel-displacements, making it more difficult to find the correct correspondence. Conversely, finding correct correspondences may become more difficult at too coarse spatial resolutions as well because visibility of anatomical features may be compromised at low resolutions. Thus, an intermediate spatial resolution is optimal for MALF applications.

TABLE 1

| MALF/MALF + CL | 1 mm | 3 mm | 5 mm |
| --- | --- | --- | --- |
| sternum | 0.743/0.764 | 0.760/0.782 | 0.683/0.749 |
| ascending aorta | 0.722/0.741 | 0.757/0.755 | 0.736/0.746 |
| descending aorta | 0.782/0.822 | 0.829/0.846 | 0.809/0.850 |
| aortic arch | 0.520/0.532 | 0.545/0.560 | 0.536/0.562 |
| aortic root | 0.513/0.531 | 0.589/0.593 | 0.550/0.578 |
| pulmonary artery trunk | 0.757/0.767 | 0.803/0.808 | 0.768/0.803 |
| pulmonary artery right | 0.830/0.842 | 0.838/0.862 | 0.787/0.845 |
| pulmonary artery left | 0.771/0.791 | 0.791/0.812 | 0.726/0.797 |
| vertebrae | 0.869/0.881 | 0.880/0.888 | 0.866/0.885 |
| right atrium | 0.794/0.823 | 0.850/0.865 | 0.831/0.861 |
| left atrium | 0.861/0.885 | 0.884/0.897 | 0.861/0.892 |
| right ventricle | 0.752/0.809 | 0.845/0.857 | 0.829/0.857 |
| left ventricle | 0.688/0.732 | 0.736/0.750 | 0.714/0.748 |

TABLE 1-continued

| MALF/MALF + CL | 1 mm | 3 mm | 5 mm |
| --- | --- | --- | --- |
| myocardium | 0.790/0.836 | 0.821/0.854 | 0.788/0.849 |
| aortic valve | 0.371/0.375 | 0.368/0.426 | 0.310/0.370 |
| pulmonary valve | 0.137/0.126 | 0.278/0.363 | 0.232/0.340 |
| tricuspid valve | 0.074/0.073 | 0.066/0.058 | 0.017/0.010 |
| mitral valve | 0.372/0.440 | 0.512/0.559 | 0.338/0.458 |
| All | 0.631/0.655 | 0.678/0.700 | 0.635/0.682 |

As shown in Table 1, segmentation accuracy (Dice similarity coefficient) was produced by MALF/MALF+CL when MALF is applied in different spatial resolutions. The results were computed by comparing automatic segmentation with manual segmentation in the 1 mm resolution space.

With corrective learning applied, the most improvement, 4.7%, is obtained when MALF is applied in 5 mm resolution. This application of MALF at a low spatial resolution produces systematic errors, which can be effectively corrected by learning-based error correction. The overall segmentation accuracy produced by applying MALF+CL at 3 mm and 5 mm resolution both out performed applying MALF+CL at 1 mm resolution.

Figure 7:
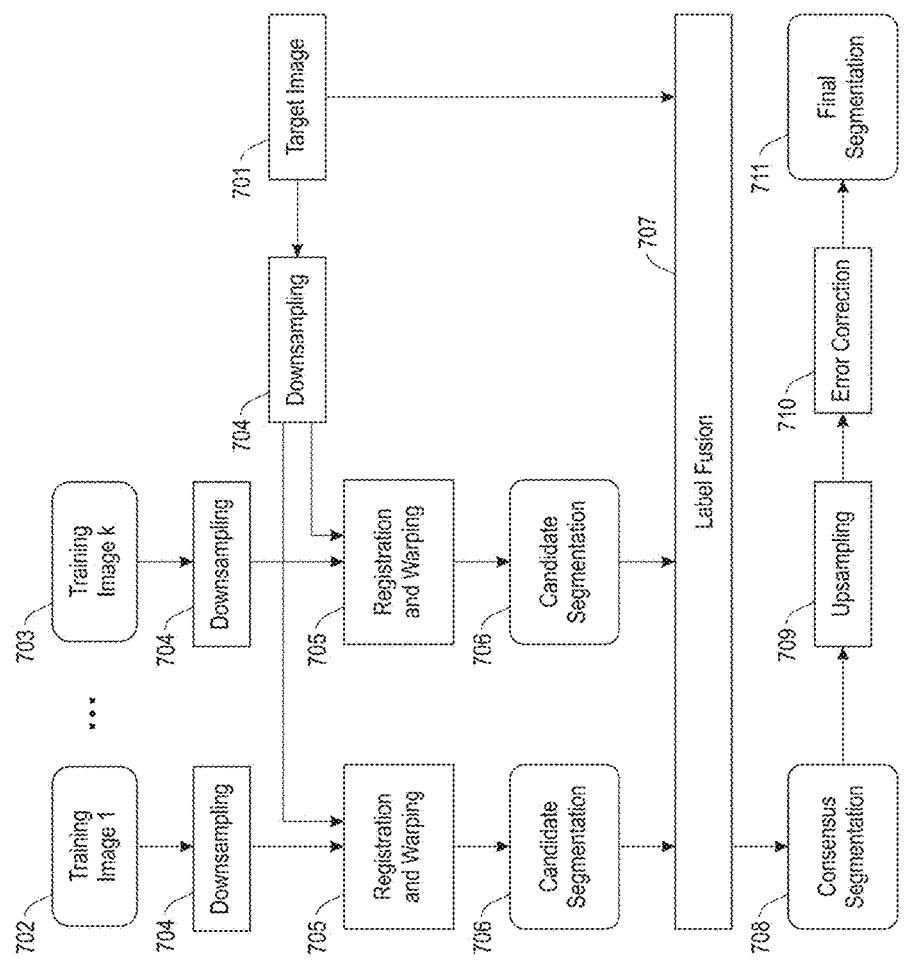
FIG. 7 illustrates an exemplary segmentation pipeline according to embodiments of the present disclosure.

Referring to FIG. 7, an exemplary segmentation pipeline according to embodiments of the present disclosure is illustrated. Target image 701, as well as training atlas images 702 . . . 703 are downsampled 704. Pairwise deformable registration 705 is applied between target image 701 and each of training atlas images 702 . . . 703. Based on the registrations, candidate segmentations 706 are produced for the target image by warping the label from each of the atlases. Joint label fusion 707 is applied to produce an initial segmentation 708 for the target image. The resulting segmentation is upsampled 709 to the original resolution of the input image. A sequential learning algorithm is applied 710 to correct segmentation errors produced by joint label fusion to generate the final output 711.

Figure 8:
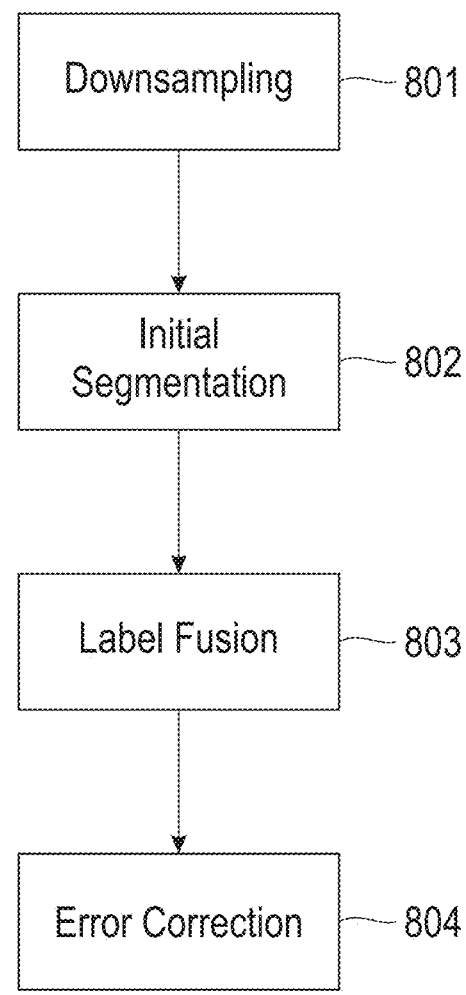
FIG. 8 illustrates an exemplary method for segmentation according to embodiments of the present disclosure.

Referring to FIG. 8, the present disclosure provides for methods to address the high computational burden of deformable registration based multi-atlas segmentation. A target image is downsampled 801 from its original high resolution image space to a low resolution space. Multi-atlas segmentation is applied 802 to produce an initial segmentation for the target image in the downsampled low-resolution space. In some embodiments, label fusion 803 is performed. The resulting segmentation is then refined by learning-based error correction 804 in the native target image space.

In a cardiac CT segmentation application, where the native imaging space has about 1 $mm^3$ spatial resolution, applying deformable registration based multi-atlas segmentation at about 5 $mm^3$ spatial resolution is about 130 times faster than applying MALF in the native (about 1 $mm^3$) resolution space. In addition to speed gains, working with a downsampled space may produce more accurate segmentation as well. This accuracy gain has two main contributing factors: subsampled space may be optimal for computing globally optimal image registrations; and segmentation errors produced by applying MALF in a downsampled space can be effectively corrected by learning-based error correction.

When low resolution MALF is applied, learning-based error correction becomes the most time consuming step. To reduce the impact, error correction may be implemented with parallelized computation to further reduce the overall processing time.

Figure 9:
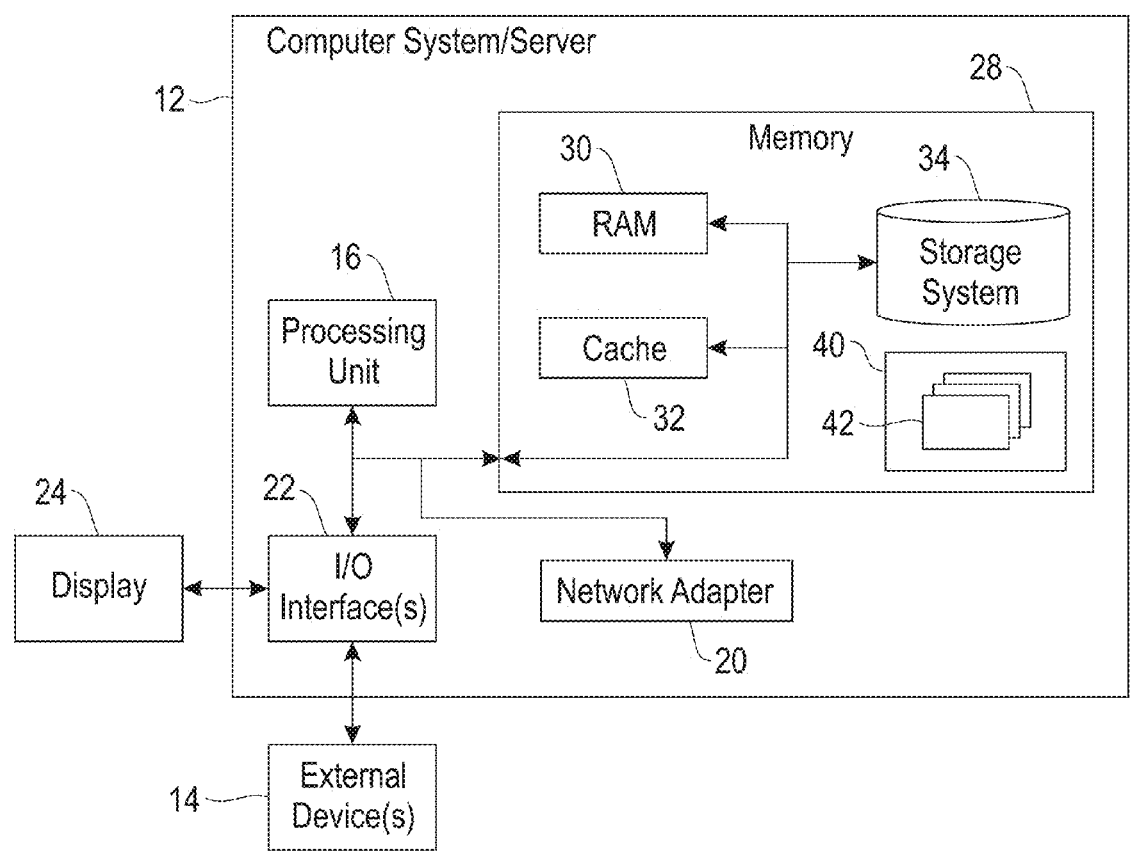
FIG. 9 depicts a computing node according to embodiments of the present invention.

Referring now to FIG. 9, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 12 in computing nodes shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Small talk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
   reading an input image, the input image having a first resolution;
   downsampling the input image to a second resolution lower than the first resolution;
   segmenting the downsampled image into a plurality of labeled anatomical segments, wherein segmenting the downsampled image comprises:
      generating a plurality of candidate segmentations by comparing the downsampled image against a plurality of training images; and
   applying error correction to the segmented image to generate an output image, the output image having the first resolution.

2. The method of claim 1, wherein generating the plurality of candidate segmentations comprises:
   registration and warping of the downsampled image.

3. The method of claim 1, wherein segmenting the downsampled image comprises:
   generating a weighted average of the plurality of candidate segmentations.

4. The method of claim 1, wherein applying error correction to the segmented image comprises:
    upsampling the segmented image from the second resolution to the first resolution.

5. The method of claim 1, wherein applying error correction comprises applying a corrective learning algorithm.

6. The method of claim 5, wherein the corrective learning algorithm comprises a random forest classifier.

7. A computer program product for anatomy segmentation, the computer program product comprising a computer readable storage medium having program instructions embodied therewith, the program instructions executable by a processor to cause the processor to perform a method comprising:
    reading an input image, the input image having a first resolution;
    downsampling the input image to a second resolution lower than the first resolution;
    segmenting the downsampled image into a plurality of labeled anatomical segments, wherein segmenting the downsampled image comprises:
        generating a plurality of candidate segmentations by comparing the downsampled image against a plurality of training images; and
    applying error correction to the segmented image to generate an output image, the output image having the first resolution.

8. The computer program product of claim 7, wherein generating the plurality of candidate segmentations comprises:
    registration and warping of the downsampled image.

9. The computer program product of claim 7, wherein segmenting the downsampled image further comprises:
    generating a weighted average of the plurality of candidate segmentations.

10. The computer program product of claim 7, wherein applying error correction to the segmented image comprises:
    upsampling the segmented image from the second resolution to the first resolution.

11. The computer program product of claim 7, wherein applying error correction comprises applying a corrective learning algorithm.

12. The computer program product of claim 11, wherein the corrective learning algorithm comprises a random forest classifier.

13. A system for anatomy segmentation, comprising one or more computing node, the one or more computing node being adapted to perform a method comprising:
    reading an input image, the input image having a first resolution;
    downsampling the input image to a second resolution lower than the first resolution;
    segmenting the downsampled image into a plurality of labeled anatomical segments, wherein segmenting the downsampled image comprises:
        generating a plurality of candidate segmentations by comparing the downsampled image against a plurality of training images; and
    applying error correction to the segmented image to generate an output image, the output image having the first resolution.

14. The system of claim 13, wherein generating the plurality of candidate segmentations comprises:
    registration and warping of the downsampled image.

15. The system of claim 13, wherein segmenting the downsampled image further comprises:
    generating a weighted average of the plurality of candidate segmentations.

16. The system of claim 13, wherein applying error correction to the segmented image comprises:
    upsampling the segmented image from the second resolution to the first resolution.

* * * * *